United States Patent [19]

Moore

[11] Patent Number: 4,991,580
[45] Date of Patent: Feb. 12, 1991

[54] METHOD OF IMPROVING THE QUALITY OF AN ELECTROCARDIOGRAM OBTAINED FROM A PATIENT UNDERGOING MAGNETIC RESONANCE IMAGING

[75] Inventor: John C. Moore, Tulsa, Okla.
[73] Assignee: Invivo Research, Inc.
[21] Appl. No.: 330,773
[22] Filed: Mar. 30, 1989
[51] Int. Cl.$^5$ .............................................. A61B 5/0402
[52] U.S. Cl. .............................. 128/696; 128/653 R; 128/653 SC
[58] Field of Search ................. 128/696, 653; 324/322

[56] References Cited

U.S. PATENT DOCUMENTS

| | | | |
|---|---|---|---|
| 3,903,874 | 9/1975 | Shakespeare | 128/696 |
| 4,694,837 | 9/1987 | Blakeley et al. | 128/671 |
| 4,763,075 | 8/1988 | Weigert | 324/318 |

Primary Examiner—Lee S. Cohen
Assistant Examiner—Kennedy J. Schaetzle
Attorney, Agent, or Firm—Head and Johnson

[57] ABSTRACT

A method for improving the quality of electrocardiogram (ECG) signals for input to a cardiac monitor and obtained from a patient undergoing magnetic resonance imaging (MRI) wherein the ECG leads attached to the patient are exposed to rapidly changing magnetic fields produced by the MRI which induce relatively high levels of rapid voltage changes in the ECG leads, the method including the steps of conducting the ECG signals having MRI induced noise signals superimposed thereon to the input of a slew rate limiter (SRL) circuit having a preselected maximum slew rate, the circuit providing an output signal having a maximum dv/dt which is slightly greater than the maximum typical ECG dv/dt, connecting the output of the SRL circuit to the input of a low pass filter circuit having an attenuation above the ECG typical fundamental frequency and connecting the output of the low pass filter circuit to a cardiac monitor.

2 Claims, 2 Drawing Sheets

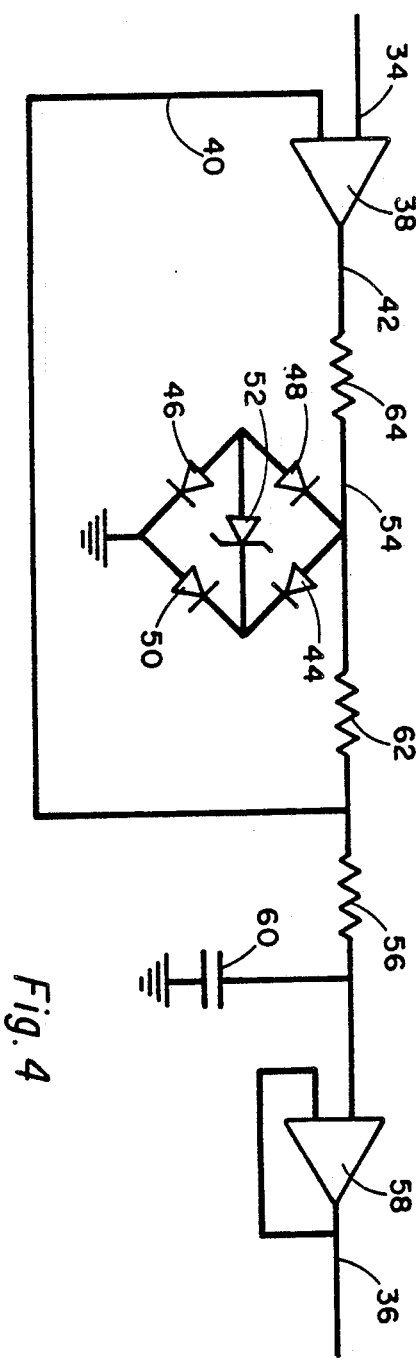
Fig.2
Fig.4
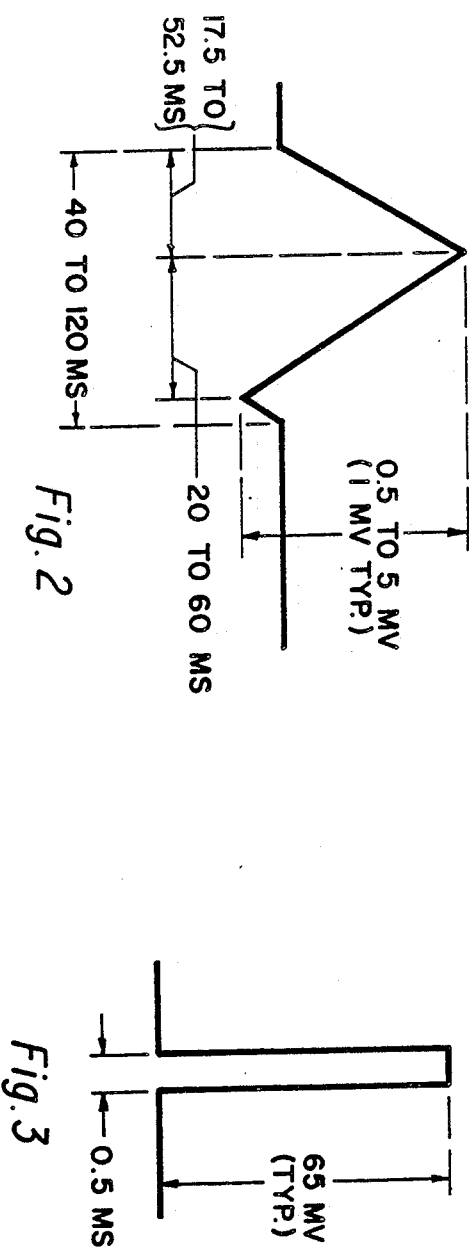
Fig.3

4,991,580

METHOD OF IMPROVING THE QUALITY OF AN ELECTROCARDIOGRAM OBTAINED FROM A PATIENT UNDERGOING MAGNETIC RESONANCE IMAGING

SUMMARY OF THE INVENTION

An important new technique utilized in medicine for investigating the condition of the human body includes the use of magnetic resonance imaging (MRI). Typically the patient is placed supine on a moveable horizontal table which moves through a field wherein the patient is subjected to rapidly changing, intense, magnetic fields. The magnetic resonance produced by the rapidly changing magnetic fields is detected and by computer analysis detailed information of the interior of the human body can be obtained which, in many instances, is more detailed than that available from X-ray and at substantially less risk to patient detriment than is occasioned by the use of X-Ray. Since obviously, most patients undergoing MRI are ill for one reason or another and since subjecting a patient to the environment by which MRI signals are derived is traumatic, it is highly desirable that the state of the physical patient be constantly monitored. For this reason, it is important that the patient's electrocardiogram (ECG) be constantly monitored during all the period the patient is undergoing MRI. The rooms in which MRI equipment is placed is typically highly shielded with monitoring equipment placed in an adjacent room. Conductors extending from attachment points on the patient are fed by a cable through the shielding to the adjacent room wherein the cardiac monitoring equipment is maintained. The shielding isolates the cardiac monitoring equipment from the high intensity magnetic fields employed in MRI, but the leads which extend from the patient and through the shielded wall are subjected to this magnetic field. The rapidly changing magnetic fields induce high level noise signals into the cardiac monitoring leads and these signals tend to obscure the normal ECG signals.

The present invention is a method of counteracting the effect of the noise signals introduced by the MRI magnetic fields in conductors extending from a patient which are used for supplying ECG signals. The method includes conducting the ECG signals having the MRI induced noise signals superimposed thereon to the input of a slew rate limiter (SRL) circuit. The slew rate limiter (SRL) circuit has a preselected maximum slew rate; that is, an output having a preselected maximum dv/dt in which the preselected maximum dv/dt is greater than the maximum typical ECG fundamental frequency dv/dt. The output from the slew rate limiter circuit is connected to the input of a low pass filter circuit having attenuation above the ECG typical fundamental frequency. The output of the filter is then connected to the cardiac monitoring equipment to produce an electrocardiogram.

In the preferred arrangement, the signals originating from the patient and carried by the conductors attached to the patient and through the shields surrounding the MRI system is first amplified before the step of conducting the superimposed signals to the input of the SLR circuit.

In the practical application of the invention, it has been found that when the SLR circuit has a maximum slew rate dv/dt of about 0.3 volt per second the noise induced by the MRI changing magnetic fields is substantially reduced so that the ECG signals can be detected to provide an accurate indication of the heart function of the patient. This dv/dt of about 0.3 V/sec. has to be adjusted when an amplification circuit is utilized in advance of the SLR. When the amplification circuit has a gain of X then the maximum slew rate dv/dt is about 0.3 X volts per second.

Further, it has been determined that a low pass filter which substantially attenuates the amplitude of signals above about 30 Hz, improves the signals to noise ratio of the input to the cardiac monitor.

A better understanding of the invention will be had to references to the following description and claims, taken in conjunction with the attached drawings.

DESCRIPTION OF THE DRAWINGS

FIG. 2 is an AAMI Standard ECG QRS pulse signal representative of the signal which is produced by a heart beat of a patient and which is to be monitored by an ECG portion of a cardiac monitor.

FIG. 3 is a typical signal induced into conductors attached to a patient undergoing MRI illustrating the intensity of the noise signals.

FIG. 4 is a diagram of a circuit embodying the principles of this invention for providing an output signals to a cardiac monitor and in which the drastic facts of the magnetically induced noise signals are attenuated so that meaningful cardiac monitoring signals are obtained.

DESCRIPTION OF THE PREFERRED EMBODIMENT

Figure 1:
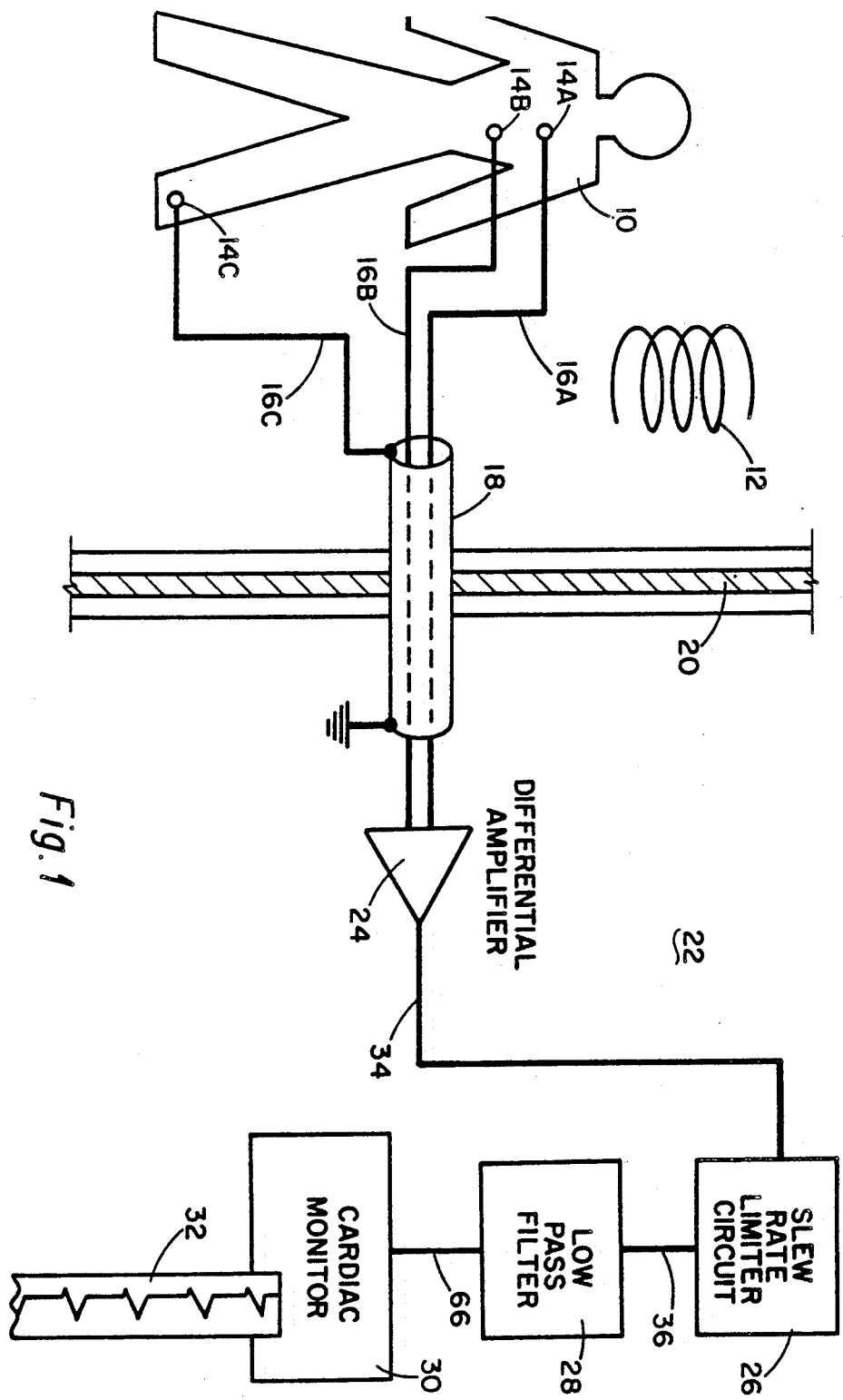
FIG. 1 is a diagrammatic representation of a patient undergoing MRI in one room, the patient having ECG leads attached to conductors extending through a shielded wall into an adjacent instrument room, and in which, in the instrument room, ECG equipment is located.

MRI is accomplished by subjecting the patient to varying magnetic fields. These varying fields are called magnetic "gradients". Large MRI's in present use employ approximately 1.5 tesla and switch the gradient fields vary quickly during a scan pattern. The magnetic field may be switched as quickly as 25 gauss in 0.5 milliseconds which is a rate of change of 50,000 gauss per second or 5 tesla per second. The patient's ECG leads are typically 8 inches in length and at least two of them are used to measure ECG voltages on the surfacers of the patient. If the electrodes are merely shorted together and the wires are formed into a loop, this loop area will equal 0.013 sq. meters. When oriented for maximum coupling, this loop will generate a voltage of 0.013 times 5 tesla/second, which equal 65 millivolts. Since there are three orthogonal gradient fields, a large percentage of this maximum voltage will normally be present at the ECG cable as gradient noise. The patient's normal ECG signal is only about 1 mv. typically, so the gradient noise pulse will be much larger than a patient's ECG signal. The gradients are changed perhaps 200 times/second. The gradient change cycles depend on how the system is scanning and many other factors. In any event, the gradient noise is much larger than the ECG signal and comes much more frequently than the ECG signal, and so unless neutralized in some way the gradient noise signals will mask an ordinary ECG system signal.

The ECG signal is limited to about 30 hertz in band width so an obvious solution would be to attempt to filter out the gradient noise with a 30 hertz linear filter. The typical gradient noise pulse as discussed above has an amplitude typically of about 65 mv. and is pulsed in about 0.5 ms. If this pulse is passed through a linear, first order 30 hertz low pass filter, the resultant pulse will have an amplitude of approximately 6 mv. In addition, the results of the filter gradient pulse will have been stretched to approximately 12 ms. in length at the 10 per cent points. This signal is many times larger than the patient's typical 1 mv. ECG signal. Even within the ideal 30 hertz low passed filter, much the same signal results but with a long ringing tail.

The Association For the Advancement Of Medical Instrumentation (AAMI) standard gives a worst case ECG wave form having maximum peak amplitude of of 4.375 mv. and minimum rise time of 17.5 ms. This gives a maximum slew rate of 0.25 volts/sec. for a worse case ECG pulse. The slew rate of the gradient noise pulse is much higher than even a worse case AAMI ECG pulse.

FIG. 2 is a representative ECG pulse referred to as the AAMI Standard ECG weave form showing the typical voltage changes produced by the typical electrical signal generated by a patient's heart beat.

FIG. 1 shows a patient 10 as positioned on a table (not shown). The patient is passed within a magnetic field indicated diagrammatically by coil 12. The patient has attached electrodes 14A, 14B and 14C for gathering ECG signals form the patient. Three electrodes are shown although a minimum of two is required, and in some cases more than three are employed. The electrodes are attached to conductors 16A, 16B and 16C which extend to a shielded cable, the shield being indicated by the numeral 18. In the illustrated arrangement electrodes 14C and conductor 16C serve as ground with the conductors 16A and 16B carrying the ECG signal.

MRI is usually carried out in a shielded room, the shield surrounding the room being diagrammatically indicated by the numeral 20. Most of the instrumentation used to record the information generated by the MRI and ancillary equipment secured to the patient such as that provided by electrodes 14A, 14B and 14C is located in an adjacent room. Portions of the electrical equipment for use in practicing the invention are connected to the shielded cable 18 within the instrument room 22, although some of the circuit components later discussed, when properly shielded, may be in the same room as the patient 10. The electrical equipment include a differential amplifier 24, a slew rate limiter circuit 26, a low pass filter circuit 28 and cardiac monitoring equipment 30. The cardiac monitoring equipment typically includes an ECG which also typically provides a chart read-out for immediate visual inspection by medical technicians, the chart being indicated diagrammatically by 32.

Referring to FIGS. 3, the typical voltage generated as a noise signal due to the rapid change of the magnetic field to which the patient 10 is subjected is illustrated. Each time the magnetic field polarity is switched, the voltage induced in conductors 16A and 16B by this changing magnetic field is indicated typically in FIG. 3. This illustrates that voltage spikes of 65 mv. within 0.5 ms. can be expected. By comparing the noise signal of FIG. 3 with the typical ECG signal of FIG. 2 it is apparent that when these signals are superimposed the ECG signal is substantially obscured. This is particularly true during periods when the magnetic fields are changed rapidly in comparison to the typical heart beat rate of the patient.

FIGS. 1 and 4 show a circuit for use in providing an improved ECG signal. The input signals from the shielded cable 18 is fed to a differential amplifier 24. The output from the differential amplifier on conductor 34 typically has a gain of 21. Because the slew rate limiter is driven by the differential amplifier 24, the signals in reference to the system input will be 1/21 of that on conductor 34.

As shown in FIG. 4, the SRL circuit input is on conductor 34 and the output on conductor 36, which conductor feeds the cardiac monitoring equipment 30 as shown in FIG. 1. The noninverting input of an operational amplifier 38 is driven by the signal on conductor 34. An inverting input to the operational amplifier 38 is provided by the signal on conductor 40. The actual value of the differential gain of the operational amplifier 38 can vary widely due to many factors, but can be depended upon to very large. As long as the circuit is in its linear range, the operational amplifier 38 will drive its output on conductor 42 to cause inverting input on conductor 40 to be very nearly equal to the input on conductor 34. Operationally amplifier 38 thus is connected in a negative feedback configuration.

The output of the operational amplifier 38 has voltage limits which are not well controlled. The negative limit may not be the same as the positive limit. A limiter circuit is included to make the positive and negative operational amplifier output limits be very close to equal. If they were not equal, there would be a difference in sew rate which would cause the modulation of any high frequency noise that happened to be present.

The slew rate limiter 26, comprised of elements 38 through 60 of FIG. 4 operates as follows: When the amplifier 38 output drives positive, diodes 44 and 46 are forward biased and diodes 48 and 50 are reverse biased. This puts the zener diode 52 in series with diodes 44 and 46 with its cathode positive and its anode negative. If the voltage on conductor 42 exceeds the zener breakdown voltage plus the two diode drops, then the voltage on conductor 54 will be limited to the zener voltage plus the 2 diode forward voltage drops. The zener voltage we used was 6.2 volts. Thus, the voltage on conductor 54 will be limited to $6.2 + 2 \times 0.6 volts = 7.4 volts$. When the voltage on conductor 42 swings negative, diodes 48 and 50 will then be forward biased and diodes 44 and 46 reversed biased, and the zener diode 52 will still see a positive voltage on its cathode and a negative voltage on its anode. So when voltage on conductor 42 swings negative, the voltage on conductor 54 will again be limited to 7.4 volts. Therefore, the limiter will limit the operational amplifier output to approximately $\pm 7.4$ volts. The positive limit will be the same as the negative limits if the four bridge diodes 44, 46, 48 and 50 are perfectly matched. In practice, they will be matched within a few millivolts. Because of the diode bridge, the zener 52 always sees a positive rectified version of the voltage on conductor 54 from its cathode to its anode.

Resistor 56 is a very small value resistor so for the present point in the explanation its effect will be considered to be zero.

The output voltage of the slew rate limiter will also be small, approximately 21 times 5 mv. max equal $\pm 0.105$ volts for the range of ECG signals. This is much smaller than the 7.4 volts of the limiter. Amplifier 58 is a unity gain buffer operational amplifier voltage buffer whose purpose is to provide a low impedance output without loading capacitor 60. The input impedance of amplifier 58 is assumed to be infinite for the purposes of this description.

The voltage limiter is followed by resistor 62 which converts the voltage at 54 from a voltage to a current. Resistor 62 is normally a large value, such as 10 megohms. Since the voltage at 54 is limited, the current is limited to about ±7.4 volts over 10 megohms or to ±0.7 microamps limit.

Since the current in capacitor 60 is related to its voltage by the relationship $I = C(dv/dt)$. Thus, for capacitor 60, $dv/dt = I/$capacitor 60. Since the current is limited to about ±0.7 microamps, the maximum slew rate for capacitor 60 is about 7 microamps/1 microfarad = ±7 volts/sec. This is the maximum rate that this circuit output will slew. When the 7 volts/sec. is referred to the system input by dividing by 21 we obtain the maximum slew rate of 0.33 volts/sec. This is the fastest that this circuit will respond to any input. From the previous discussion, according to the AAMI Standard ECG Wave Form, the maximum slew rate for such signals is 0.25 volts/sec. at the ECG leads, that is, the system input. Therefore, the ECG signal is not limited by the slew rate of 0.33 volts/sec.

For normal ECG signals, operational amplifier 38 is able to drive the output at 42 in order for the input at conductor 40 to very nearly equal the input at 34 without any limiting action. Since normal dv/dt is less than 7 volts/sec, consequently I is less than 0.74 microamps and consequently the voltage at 54 is less than ±7.4 volts so the zener diode does not see enough voltage for it to reach zener break down so it is in a high impedance state and not limiting occurs at 54. Since there is negligible current through the zener diode 52, voltage at 44 is substantially the same as the voltage at 42. So for normal ECG signals, no limiting occurs and the diode bridge and zener diode are out of the circuit. Under these conditions, the capacitor 60 is effectively driven by resistor 64 which typically is 4.7 K ohms = 10 megohms = 100 ohms or approximately 10 megohms. This gives a linear low pass filter consisting of a 10 megohms resistor and capacitor 60 having a low frequency cutoff. It also adds approximately 90° of phase shift at high frequencies which tends to unstabilize the operational amplifier feedback loop at high frequencies. Resistor 56 is added to improve the feedback loop's stability at high frequencies since it provides compensating phase shift beginning at 15.9 Khz to cancel the 90° phase shift in the low pass filter consisting of the 10 megohm and capacitor 60. Therefore the only purpose of resistor 56 is to improve loop stability.

The slew rate limiter circuit does not affect the ECG wave form—it only affects the gradient noise pulses so in effect it is a non-linear filter that discriminates against the gradient noise pulses. When the gradient noise pulse is passed through the slew rate limiter there is a large effect. When the noise pulse is applied, the slew rate limiter slews at its maximum rate of about 0.33 volts per second. The result is a triangular output which peaks at the end of the noise pulse and reaches an amplitude of (slew rate) X (noise pulse duration)=0.33v/sec×0.5ms=0.17mv. This is a very substantial reduction in the noise pulse. Since the resulting pulse out of the slew rate limiter is trianugular, it has even less energy than would a square pulse of the same amplitude, so that the actual noise reduction is even greater. The output of the slew rate amplifier is improved by passage of the signal through a low pass filter 28 as shown in FIG. 1 for the signal is passed from the low pass filter on conductor 66 to the cardiac monitoring equipment 30. The low pass filter preferably is designed to substantially attenuate the amplitude of signals above about 30 hertz. The combination of the slew rate limiter and low pass filter function to provide an output signal dominated by the ECG signal derived from the patient and for driving the cardiac monitor 30.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A method of improving the quality of electrocardiogram (ECG) signals for input to a cardiac monitor and obtained from a patient undergoing magnetic resonance imaging (MRI) wherein the ECG leads attached to the patient are exposed to changing magnetic fields produced by the MRI which induce relatively high levels of rapid voltage changes in the ECG leads, comprising:

conducting the ECG signals having MRI induced noise signals superimposed therein to the input of a slew rate limiter (SRL) circuit having a preselected maximum slew rate, the circuit providing an output signals having a maximum dv/dt which is slightly greater than the maximum typical ECG dv/dt;

amplifying the ECG signal having the MRI induced noise superimposed thereon;

connecting the amplified output of the SRL circuit to the input of a low pass filter (LPF) circuit having attenuation above the ECG typical fundamental frequency; and connecting the output of the LPF circuit to a cardiac monitor, wherein said step of amplifying the ECG signal having the MRI induced noise superimposed thereon has a gain of X and wherein said SRL maximum slew rate dv/dt is about 0.3 X v/sec.

2. A method according to claim 1 wherein the LPF substantially attenuate the amplitude of signals above about 30 Hz.

* * * * *